(12) United States Patent
Wippenbeck et al.

(10) Patent No.: US 11,971,341 B2
(45) Date of Patent: Apr. 30, 2024

(54) METHOD AND DEVICES FOR ANALYZING SPERM SAMPLES

(71) Applicant: MINITÜB GMBH, Tiefenbach (DE)

(72) Inventors: Georg Wippenbeck, Aham (DE); Christian Simmet, Landshut (DE)

(73) Assignee: MINITÜB GMBH, Tiefenbach (DE)

(*) Notice: Subject to any disclaimer, the term of this patent is extended or adjusted under 35 U.S.C. 154(b) by 1449 days.

(21) Appl. No.: 16/196,479

(22) Filed: Nov. 20, 2018

(65) Prior Publication Data
US 2019/0195770 A1    Jun. 27, 2019

(30) Foreign Application Priority Data
Dec. 22, 2017    (EP) .................... 17210219

(51) Int. Cl.
| | |
|---|---|
| *B01L 3/00* | (2006.01) |
| *C12Q 1/06* | (2006.01) |
| *G01N 15/06* | (2006.01) |
| *G01N 15/10* | (2006.01) |
| *G01N 15/14* | (2006.01) |
| *G01N 15/1404* | (2024.01) |
| *G01N 21/03* | (2006.01) |
| *G02B 21/34* | (2006.01) |
| *G02B 21/16* | (2006.01) |

(52) U.S. Cl.
CPC ........ *G01N 15/1404* (2013.01); *B01L 3/5027* (2013.01); *C12Q 1/06* (2013.01); *G01N 15/06* (2013.01); *G02B 21/34* (2013.01); *B01L 2200/021* (2013.01); *B01L 2200/026* (2013.01); *B01L 2200/14* (2013.01); *G01N 2015/0693* (2013.01); *G01N 2015/1006* (2013.01); *G01N 2015/1486* (2013.01); *G01N 2201/0662* (2013.01); *G02B 21/16* (2013.01)

(58) Field of Classification Search
None
See application file for complete search history.

(56) References Cited

U.S. PATENT DOCUMENTS

| | | | | |
|---|---|---|---|---|
| 4,911,782 A | * | 3/1990 | Brown ................. | B01L 3/5027 216/48 |
| 6,552,784 B1 | * | 4/2003 | Dietz .................. | G01N 21/645 436/526 |

(Continued)

FOREIGN PATENT DOCUMENTS

| | | |
|---|---|---|
| EP | 3199937 A1 | 8/2017 |
| WO | 2014038399 A1 | 3/2014 |

OTHER PUBLICATIONS

Office Action dated Jan. 13, 2020 by the European Patent Office in the parallel European Patent Application No. 17210219.6, which the subject application claims priority.

*Primary Examiner* — Neil N Turk
(74) *Attorney, Agent, or Firm* — SALIWANCHIK, LLOYD & EISENSCHENK

(57) ABSTRACT

The present invention relates to a method for analyzing samples comprising spermatozoa, said method comprising the use of a flow-through counting compartment, wherein the time period between the end of loading and closing is carried out in a controlled and specified time period. The present invention further relates to a counting compartment or chamber suitable for said method and to a counting device comprising said counting compartment.

12 Claims, 8 Drawing Sheets

(56) References Cited

U.S. PATENT DOCUMENTS

| | | | |
|---|---|---|---|
| 8,852,524 B2* | 10/2014 | Guo | G02B 21/34 435/970 |
| 2004/0180397 A1* | 9/2004 | Chang | G01N 35/00029 435/40.5 |
| 2007/0026469 A1* | 2/2007 | Fuchs | B01L 3/502761 435/7.23 |
| 2008/0287830 A1* | 11/2008 | Voeller | G01N 33/49 600/573 |
| 2015/0118708 A1 | 4/2015 | Hammond et al. | |

* cited by examiner

METHOD AND DEVICES FOR ANALYZING SPERM SAMPLES

CROSS-REFERENCE TO A RELATED APPLICATION

This application claims priority to European Patent Application No. EP 17210219.6, filed Dec. 22, 2017; which is incorporated herein by reference in its entirety.

FIELD OF THE INVENTION

The present invention relates to a method for analyzing samples comprising spermatozoa, said method comprising the use of a flow-through counting compartment, wherein the time period between the end of loading and closing is carried out in a controlled and specified time period. The present invention further relates to a counting compartment or chamber suitable for said method and to a counting device comprising said counting compartment.

BACKGROUND OF THE INVENTION

When examining body fluids, it is often desirable to study samples of such biological material under the microscope over a certain time. In particular, when examining sperm, the aim is to establish how many spermatozoa are present in the sample and also how motile they are and how their morphology is.

To carry out this investigation, a sample of a certain thickness is to be subjected to microscopic examination in a counting compartment. This counting compartment is usually provided by means of a counting chamber where two glass plates are attached to another at a given distance. The spermatozoa can then either be counted by means of a computer-assisted sperm analysis system which uses a camera and image analysis software to determine the number of sperm per unit volume sample liquid or manually by a skilled lab technician using a grid built into the eye lens of the microscope. Such a grid may be divided into a hundred squares, and the number of cells (such as spermatozoa) in each of a representative number of squares can be counted by the investigator in order to determine the total number of cells in the whole grid area. Such a grid may also be provided in the counting compartment. Both computer-assisted analysis system and operator usually count the number of sperm in several fields of the counting compartment in order to count a representative distribution of the sperm contained in the sample size. Assessment of the motility of a sample containing spermatozoa of a mammalian species requires that the counting compartment is heated to a specific temperature suitable to stimulate the motility of the sperm of that species. Typically this temperature is between 37 and 40° C.

From U.S. Pat. Nos. 4,911,782 and 5,200,152 a method is known for conducting such determinations with the aid of a counting compartment formed by two transparent plates joined together by a connecting layer composed of a cured plastic.

From U.S. Pat. No. 6,551,554 B1 and EP patent No. 0 809 815 B1 a counting device is known, which comprises two transparent plates which are held at a fixed distance from each other and joined together by a connecting layer, and at least one counting compartment which is situated between the plates, bounded by the connecting layer and fitted with an inlet and an outlet. The connecting layer contains material particles which are separate from one another and have a size that determines the depth of the counting compartment, which material particles are substantially in contact with the two plates.

For a correct quantitative evaluation of a sample it is required that the correct depth between the two glass plates of the counting device is maintained throughout the complete counting area. It is also required that there is no variation between counting devices in order to allow a correct quantitative evaluation of all samples to be analyzed using such a device. However, this counting device is a one-way device and requires a new counting area for each sample thus raising high requirements for uniformity of the devices. The way of loading the device as well as the quality of the sample can influence the result of such an evaluation. As the two glass plates are firmly attached to each other, the sample must pass through a very small gap into the counting area (typically between 10 and 100 µm), being thus exposed to any kind of blocking or sieving effects developing at such a small gap. The qualitative analysis of a sample of cells, in particular sperm, requires a completely inert and non-toxic environment to allow observation of unimpaired motility and morphology of the sperm. Typically counting devices consisting of two glass plates use a glue or adhesive to attach the glass plates to each other. Such binding material often is toxic to sperm and impairs motility and or morphology of the sperm.

There is a need in the art for improved methods and means for analysing samples comprising spermatozoa, which in particular allow obtaining accurate and improved measurement results.

SUMMARY OF THE INVENTION

According to the present invention this object is solved by a method for analyzing samples comprising spermatozoa, said method comprising the steps of (1) providing a sample comprising spermatozoa to be analyzed, which is preferably homogenized;
(2) providing a counting compartment, said counting compartment comprising
  (a) a movable lid or top part comprising a top measurement window;
  (b) a bottom part comprising a bottom measurement window, said bottom part being optionally movable;
  (c) at least two different depths provided by the bottom and top measurement window in the range of about 5 to about 100 µm, preferably about 10 µm to 40 µm, wherein the at least two different depths provided by the bottom and top measurement window are achieved by
    (i) the bottom and/or top measurement window comprise step(s); or
    (ii) one of the bottom or top measurement window is placed with inclination; or
    (iii) one of the bottom or top measurement window is placed parallel to the other measurement window and is provided with an inclined plane on the side facing the sample liquid; or
    (iv) moving the lid or top part and/or the bottom part of the counting compartment,
  (d) means for moving the lid or top part;
  (e) an inlet and outlet;
  (f) a heating unit, and
  (g) a positioning unit.
(3) loading the counting compartment with the sample, wherein the lid or top part is in open position;
(4) closing the counting compartment by closing the lid or top part;

wherein the time period between the end of the loading step (3) and the closing step (4) is less than 1 s, preferably equal to or less than about 500 ms,
(5) determining a sample value to be measured at the first depth of the at least two different depths,
  optionally, determining further sample characteristics at said first depth of the at least two different depths;
(6) optionally, determining further sample characteristics at the second depth of the at least two different depths,
(7) opening the counting compartment by opening or lifting the lid or top part;
(8) rinsing the counting compartment and thereby removing the sample,
wherein the sample value to be measured in step (5) is the number of spermatozoa or concentration of spermatozoa.

According to the present invention this object is solved by a counting compartment for analyzing samples comprising spermatozoa, said counting compartment comprising:
  (a) a lid or top part comprising a top measurement window, said lid or top part being optionally movable;
  (b) a bottom part comprising a bottom measurement window, said bottom part being optionally movable;
  (c1) at least two different depths provided by the bottom and top measurement window in the range of about 5 to about 100 µm, preferably about 10 µm to 40 µm,
    wherein the at least two different depths provided by the bottom and top measurement window are achieved by
    (i) the bottom and/or top measurement window comprise step(s); or
    (ii) one of the bottom or top measurement window is placed with inclination; or
    (iii) one of the bottom or top measurement window is placed parallel to the other measurement window and is provided with an inclined plane on the side facing the sample liquid; or
    (iv) moving the lid or top part and/or the bottom part of the counting compartment,
  (c2) at least one further depth which is different from the at least two depths of (c1), said at least one further depth being preferably bigger, such as in the range of about 100 to about 500 µm, and being located in the counting compartment or in the area of the measuring window;
  (d) optionally, means for moving the lid or top part;
  (e) an inlet and outlet;
  (f) a heating unit, and
  (g) a positioning unit.

According to the present invention this object is solved by a counting device for analyzing samples comprising spermatozoa, said counting device comprising
  the counting compartment of the present invention,
  a control unit,
  filling means,
  removing means,
  a light microscope and/or a fluorescence microscope, preferably a phase contrast microscope,
  preferably comprising a motorized positioning unit, and/or a heating unit, optionally, sensor(s),
  such as
    white-light interferometer sensor,
    current sensor,
    inductive sensor,
    capacitive sensor, or
    optical sensor,
  and
  processing, analyzing and/or evaluating system and software.

DESCRIPTION OF THE PREFERRED EMBODIMENTS OF THE INVENTION

Figure 1:
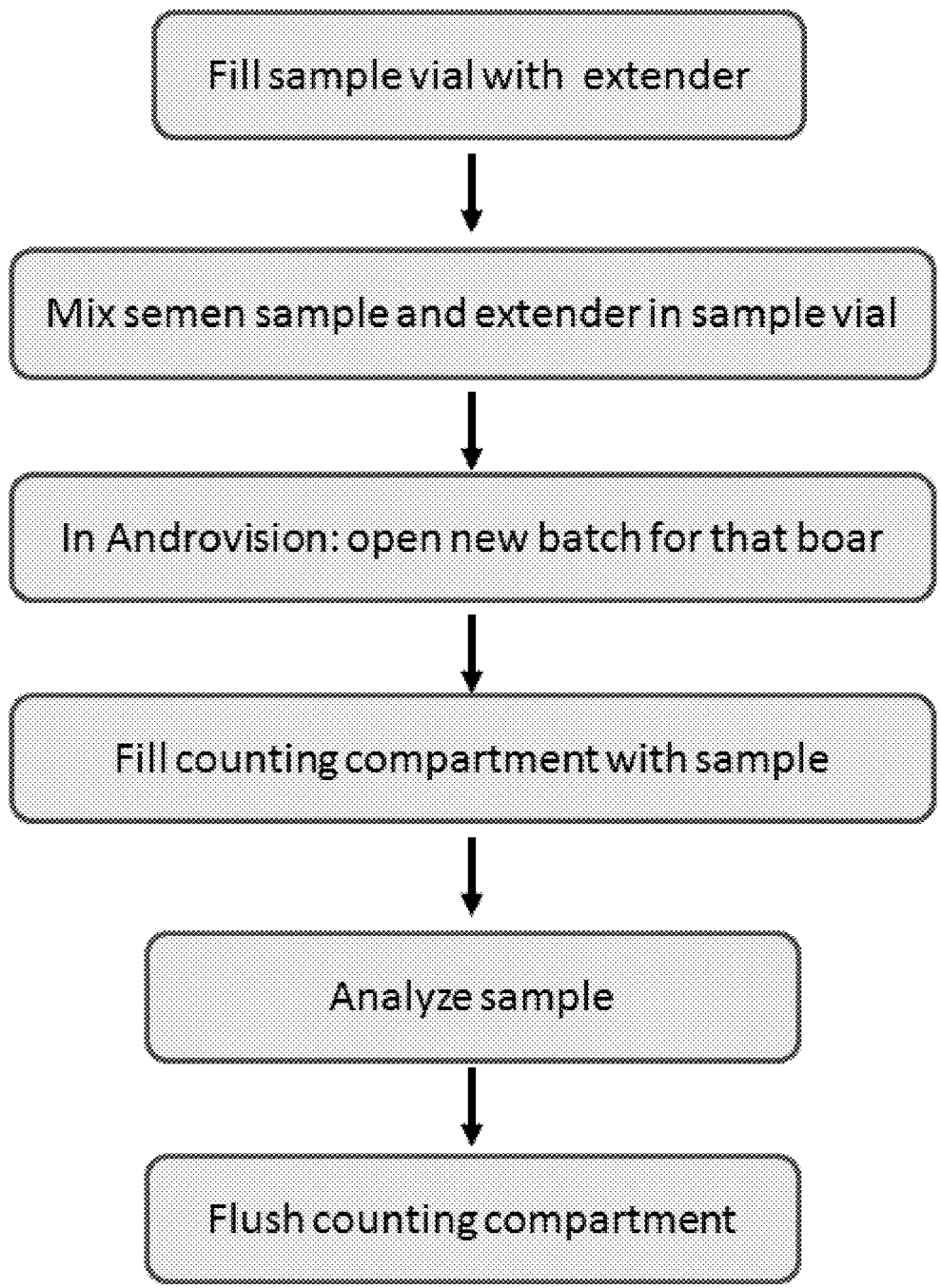
FIG. 1. Flow chart of a sperm sample analysis utilizing the method of the invention FIGS. 2A-2D. Schematic presentation of the counting compartment with at least two different depths.
(A) In one embodiment, the bottom and top measurement windows (201, 101) each comprise a step. The counting compartment is configured such that when the lid/top part (10) closes on the bottom part (20), the step of each of both measurement windows (201, 101) is on top of each other (i.e., super-imposed), thereby forming two different depths.
(B) In one embodiment, one of the bottom or top measurement windows (201, 101) is placed with inclination.
(C) In one embodiment, one of the bottom or top measurement windows (201, 101) is placed parallel to the other measurement window and is provided with an inclined plane (1000) on the side facing the sample liquid.
(D) In one embodiment, the at least two different depths are provided by movement, such as with a spindle with motor (30).

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "5 to 100" should be interpreted to include not only the explicitly recited values of 5 to 100, but also include individual values and sub-ranges within the indicated range. Thus, included in this numerical range are individual values such as 5, 6, 7, 8, 9, 10, 11, 12, 13 . . . 97, 98, 99, 100 and sub-ranges such as from 10 to 40, from 12 to 17 and 41 to 50, etc. This same principle applies to ranges reciting only one numerical value, such as "about 10". Furthermore, such an interpretation should apply regardless of the breadth of the range or the characteristics being described. Also it is to be understood that ranges may differ depending on the institute/facility where the measurements are being performed, methodology of measurement, type of tissue, and technique of tissue collection.

Methods for Analyzing Samples Comprising Spermatozoa

The present invention provides a method for analyzing samples comprising spermatozoa.

Said method comprises the steps of:
(1) providing a sample comprising spermatozoa to be analyzed;
(2) providing a counting compartment
(3) loading the counting compartment with the sample, wherein the lid or top part is in open position;
(4) closing the counting compartment by closing the lid or top part;
(5) determining a sample value to be measured at the first depth of the at least two different depths,
    optionally, determining further sample characteristics at said first depth of the at least two different depths;
(6) optionally, determining further sample characteristics at the second depth of the at least two different depths,
(7) opening the counting compartment by opening or lifting the lid or top part;
(8) rinsing the counting compartment and thereby removing the sample, After one measurement cycle, i.e. after rinsing the counting compartment (step (8)), the next sample can be analyzed.

The samples are preferably semen samples.

The sample provided in step (1) is preferably homogenized.

The inventors have found that the time period for loading a counting compartment (preferably a flow-through counting compartment) with a sperm sample and closing said compartment and for starting the measurement step (5) has to be controlled and, thus, carried out in a specified time period.

According to the invention, the time period between the end of the loading step (3) and the closing step (4) is less than 1 s, preferably equal to or less than about 500 ms, The time period between the end of the loading step (3) and the closing step (4) is less than 1 s, preferably equal to or less than about 500 ms. Thus, the closing step (4) either occurs when sample liquid is still flowing into the counting compartment or immediately after the sample flow has come to a standstill.

In a preferred embodiment, the determining of the first sample value in step (5) can start less than 1 s, preferably at about 500 ms or less than about 500 ms after the loading of the counting compartment.

In one embodiment, said time period between the end of the loading step (3) and the closing step (4), which is less than 1 s, is in the range of 0 to 500 ms, preferably 0 to 400 ms, more preferably 0 to 300 ms or less.

According to the invention, a sample value to be measured in the measurement step (5) is the number of spermatozoa or the concentration of spermatozoa in the sample.

Optionally, further sample characteristics can be determined. Said further sample characteristics can be determined at said first depth of the at least two different depths (in step (5)) and/or at the second depth of the at least two different depths.

Said further sample characteristics, optionally determined in step (5) and/or (6), can be qualitative characteristics of the sperm contained in the sample or morphological characteristics of the sperm, or combinations thereof, such as
  cell motility,
  cell morphology,
  cell viability,
  cell acrosome integrity,
  cell mitochondrion activity, and/or
  cell deoxyribonucleic acid integrity.

In a preferred embodiment: at the first depth (preferably the bigger depth), the number of spermatozoa or the concentration of spermatozoa is determined and the motility patterns; at the second depth (preferably the smaller depth), morphological analysis is carried out.

Such characteristics may be used to classify cells and determine whether or not a cell is to be counted towards the number of cells to be measured. For example, a spermatozoon, which is immobile or not viable, may, in one embodiment, not be counted towards the number of cells to be measured. Depending on the chosen characteristics/parameters, different subsets of cells in a sample may be counted.

In one embodiment of the method, the number of spermatozoa is measured by identifying and counting each sperm cell in the sample individually and, optionally, by determining, for each sperm cell individually, based on defined parameters, such as cell motility, cell morphology, cell viability etc., whether or not such cell is to be added towards the number of cells to be measured or whether or not such cell is to be added towards the number of cells of a given subpopulation of the sperm in said sample, like the number of sperm showing motility and no morphological anomaly.

The method according to the present invention is particularly suitable to count the number of spermatozoa in a sample, such spermatozoa being characterized by a set of defined characteristics, as determined by a user/operator. The characteristics may be chosen depending on the intended use of the sperm cells.

In one embodiment, the method according to the present invention neither involves the lysis of sperm cells nor the numerical determination of an absorbance value caused by an analyte/biomolecule dissolved in the (liquid) sample. In one embodiment, the method according to the present invention does not involve the numerical determination of a light scattering value caused by an analyte or cell or particle in the (liquid) sample.

The number of cells or particles is preferably an integer value.

Counting Compartment Used in the Method

The counting compartment provided in step (2) of the method comprises:
(a) a movable lid or top part comprising a top measurement window;
(b) a bottom part comprising a bottom measurement window, said bottom part being optionally movable;
(c) at least two different depths provided by the bottom and top measurement window in the range of about 5 to about 100 µm,
(d) means for moving the lid or top part;
(e) an inlet and outlet;
(f) a heating unit, and
(g) a positioning unit.

In a preferred embodiment, the counting compartment is a flow-through counting compartment.

The at least two different depths provided by the bottom and top measurement window are achieved by
(i) the bottom and/or top measurement window comprise step(s); or
(ii) one of the bottom or top measurement window is placed with inclination; or
(iii) one of the bottom or top measurement window is placed parallel to the other measurement window and is provided with an inclined plane on the side facing the sample liquid; or
(iv) moving the lid or top part and/or the bottom part of the counting compartment.

Further details for embodiments (i) to (iv) are described below. Examples are shown in FIG. 2.

The at least two different depths provided by the bottom and top measurement window are in the range of about 5 to about 100 µm, preferably about 10 µm to 40 µm, for example about 15 µm and about 30 µm, or about 10 µm and about 20 µm.

In one embodiment, the counting compartment comprises said two different depths, which are in the range of about 5 to about 100 µm (such as about 15 µm and about 30 µm); and the counting compartment comprises at least one further depth which is different from the (at least) two depths.

Said at least one further depth is preferably bigger, such as in the range of 100 to 500 µm, e.g. about 200 µm.

Figure 6A:
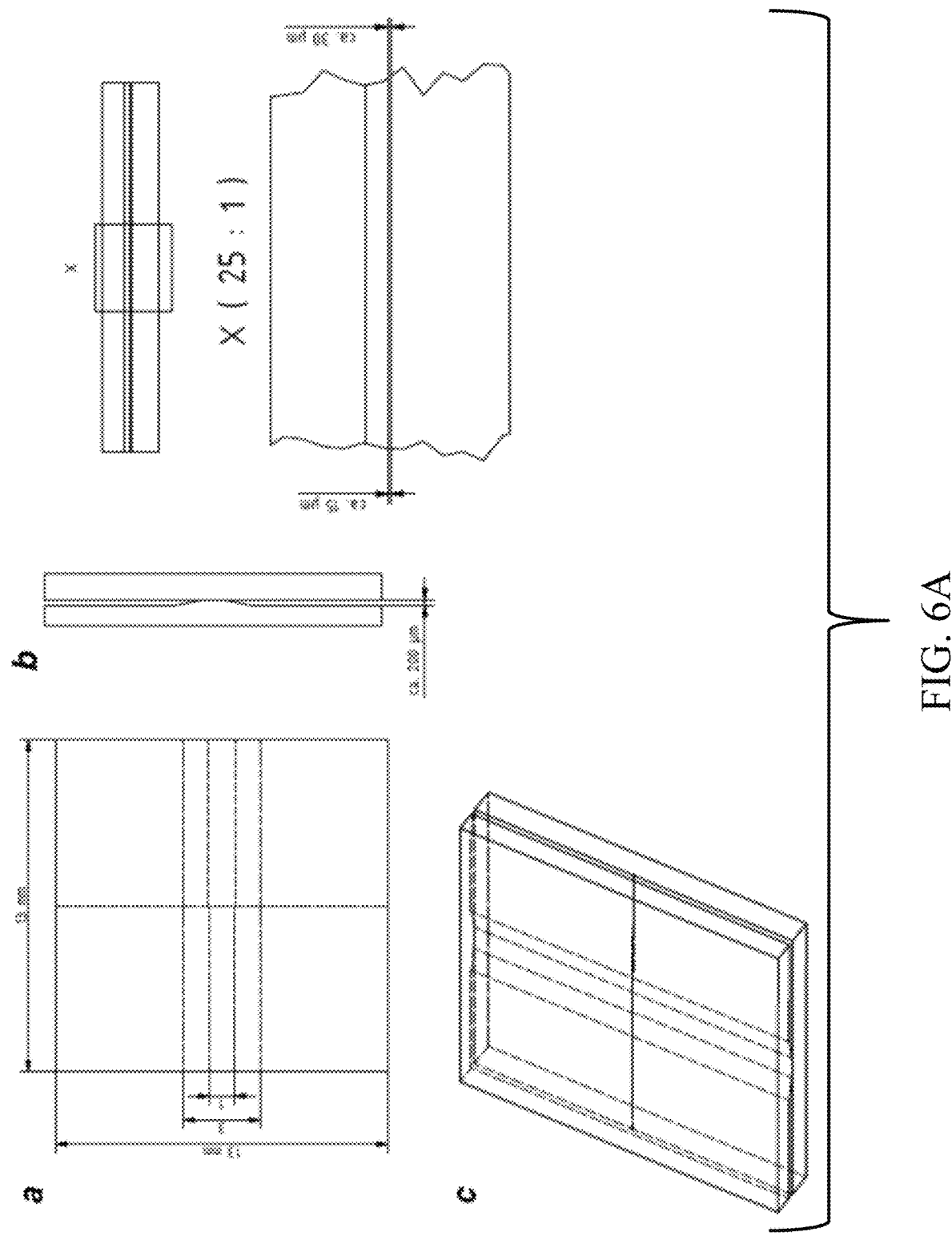
FIGS. 6A-6B. Schematic presentation of the top and bottom measurement windows of counting compartments with more than two different depths.
(A) Shown are the top view (a), and side views (b) of the top and bottom measurement windows, as well as a total view thereof (c). Furthermore, a close-up of one of the side views is shown in (b).
(B) Shown are the top view (a), a side view, including a close-up (b) of the top and bottom measurement windows, as well as a total view thereof (c).
Shown is also, that in said embodiment there are rectangular measurement fields provided by the trapezoid protrusions, with sides/edges of about 1 mm.
In both embodiments (A) and (B), the design of the top and bottom measurement windows results in the two different depths of, for example, about 15 µm and about 30 µm (for carrying out the measurement of the sample values), as well as a third depth of, for example, about 200 µm. Said third depths allows reducing/minimizing any capillary effects or other flow effects, and a simpler cleaning.
Figure 6B:
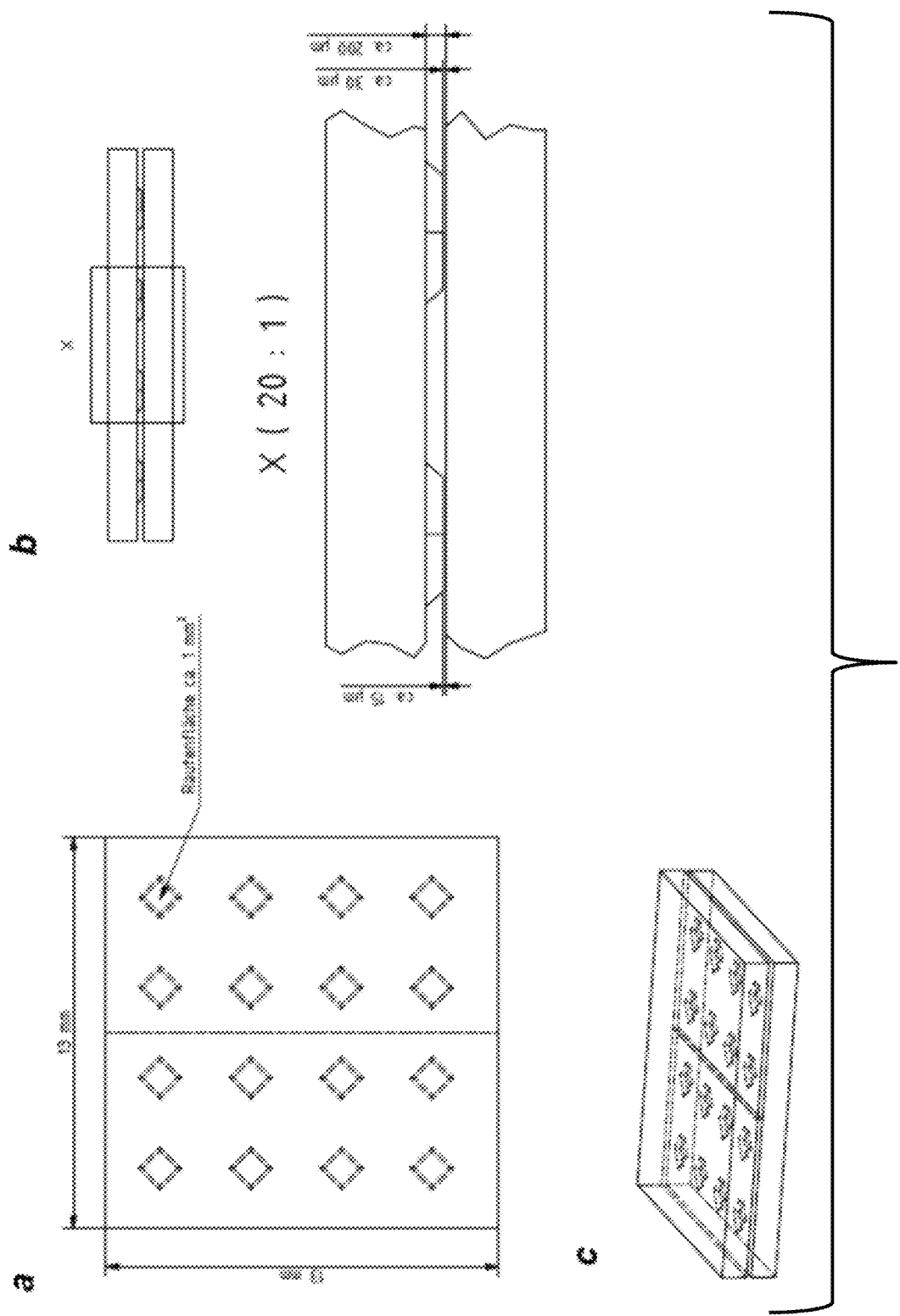

Examples are shown in FIGS. 6A and 6B.

In one embodiment, the means for moving the lid or top part (d) comprise magnetic means and optionally one or more spacers.

Preferably, the bottom window or the top measurement window are made of a transparent material, such as glass or plastic.

The counting compartment can further comprise means for controlling the depth of said counting compartment, preferably sensor(s) and/or means for z axis-calibration.

In one embodiment, the counting compartment is a component of a counting device, said counting device comprising
said counting compartment,
a control unit,
filling means,
removing means,
a light microscope and/or a fluorescence microscope, preferably a phase contrast microscope,
preferably comprising a motorized positioning unit, and/or a heating unit, optionally, sensor(s),
such as
a white-light interferometer sensor,
current sensor, inductive sensor,
capacitive sensor, or
optical sensor,
and
processing, analyzing and/or evaluating system and software, The counting device is preferably (fully) automated.

Control of the Depth

In one embodiment of the method of the invention, the at least two different depths of the counting compartment are controlled by using a dye, such as an azo dye.

For example, the counting compartment is used on a light microscope with camera and in connection with image analysis software. The counting compartment is in a first step (1) filled with a transparent liquid (such as boar semen extender BTS), closed and an image taken on the side with the greater depth between the two transparent plates. The grey value of said picture is recorded. In a second step (2) the counting compartment is emptied and filled with a liquid containing a azo dye, preferably a red azo dye, closed and an image taken on the side with the greater depth as well as the smaller depth between the two transparent plates. The grey values are proportional to the light intensity which allows the calculation of the depth of the counting chamber based on the law of Lambert-Beer:

$$E = \log_{10}\left(\frac{I_0}{I}\right) = \varepsilon \cdot c \cdot d$$

wherein:
E: Extinction
I0: Intensity of the not weakened light
I: Intensity of the weakened light
ε: Material constant
c: Concentration of the dye
d: depth of the counting compartment Material and concentration of the dye are considered constant. By taking the measurement in the transparent liquid as base value and knowing the exact difference between the greater and the smaller depth of the counting compartment, such as about 15 µm, it is possible to determine the absolute value of the depth of the counting compartment on both sides.

For further details of the flow-through counting compartment and its components, see below, in particular the following section.

Counting Compartment and Respective Counting Device

The present invention provides a counting compartment or counting chamber for analyzing samples comprising spermatozoa.

The counting compartment of the present invention is designed for the manual or automated use.

Further, it can be provided as
a flow-through compartment or
a compartment for discontinuous use (i.e. load, measure, clean and reassemble).

Said counting compartment comprises:
(a) a lid or top part comprising a top measurement window, said lid or top part being optionally movable;
(b) a bottom part comprising a bottom measurement window, said bottom part being optionally movable;
(c1) at least two different depths provided by the bottom and top measurement window in the range of about 5 to about 100 μm, preferably about 10 μm to 40 μm,
(c2) at least one further depth which is different from the at least two depths of (c1), said at least one further depth being preferably bigger, such as in the range of about 100 to about 500 μm, and being located in the counting compartment or in the area of the measuring window;
(d) optionally, means for moving the lid or top part;
(e) an inlet and outlet;
(f) a heating unit, and
(g) a positioning unit.
(a) and (b) Preferably, the bottom and/or top measurement window is made of a transparent material, such as glass or plastic.

Different Depths (c1) The at least two different depths provided by the bottom and top measurement window are achieved by
(i) the bottom and/or top measurement window comprise step(s); or
(ii) one of the bottom or top measurement window is placed with inclination; or
(iii) one of the bottom or top measurement window is placed parallel to the other measurement window and is provided with an inclined plane on the side facing the sample liquid; or
(iv) moving the lid or top part and/or the bottom part of the counting compartment.

In one embodiment (embodiment (i)), the bottom and/or top measurement window comprise step(s).

One or both of the measurement windows comprise a step. The counting compartment can be configured such that when the lid/top part closes on the bottom part the step of each of both measurement windows is on top of each other (i.e. super-imposed), thereby forming two different depths; or they are not on top of each other, thereby forming more than two different depths.

Figure 2A:
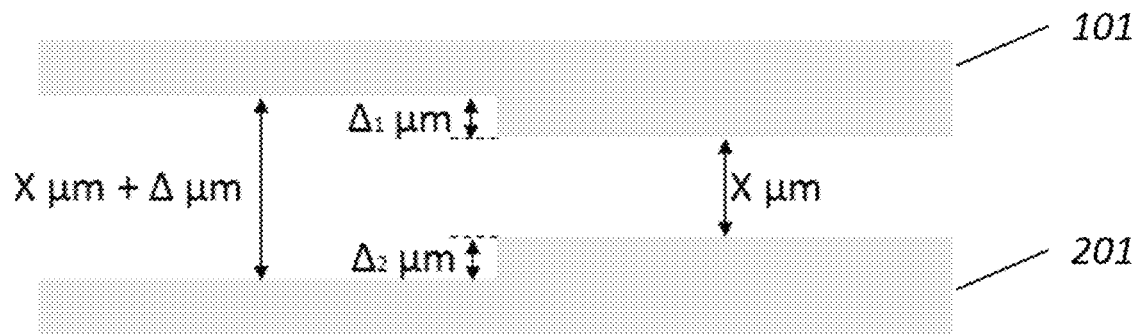

See for example FIG. 2A.

The measurement windows can also comprise more than one such step.

In one embodiment (embodiment (ii)), one of the bottom or top measurement window is placed with inclination.

Figure 2B:
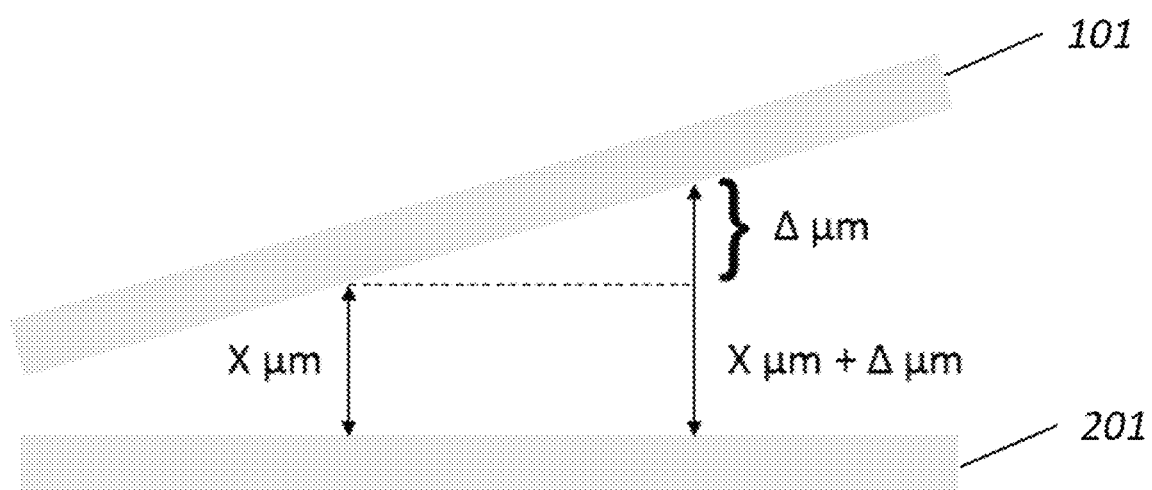

See for example FIG. 2B.

In one embodiment (embodiment (iii)), one of the bottom or top measurement window is placed parallel to the other measurement window and is provided with a inclined plane on the side facing the sample liquid.

Figure 2C:
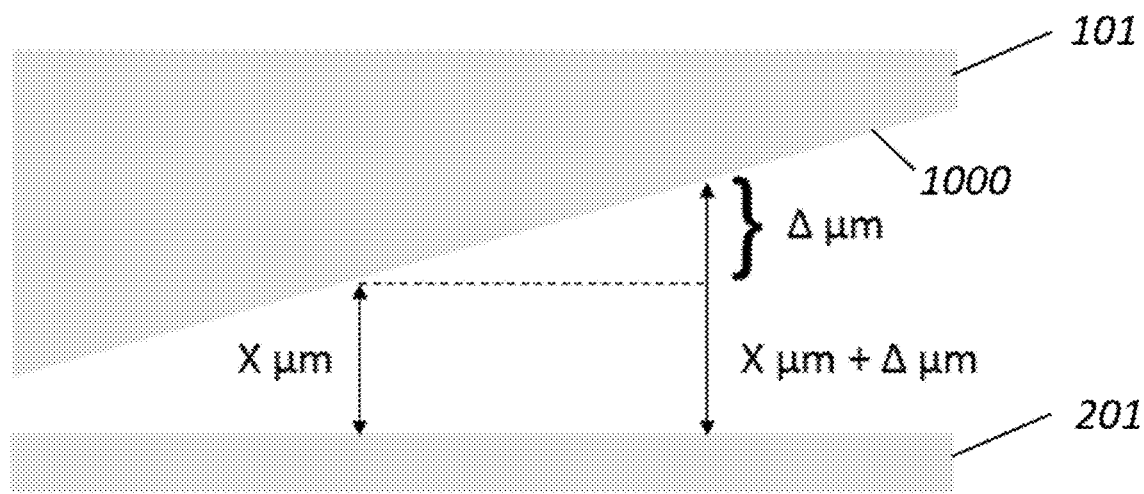

See for example FIG. 2C.

Furthermore, the at least two different depths of the counting compartment can also be provided by movement, namely by moving the lid or top part and/or the bottom part of the counting compartment, such as with a spindle with motor.

Figure 2D:
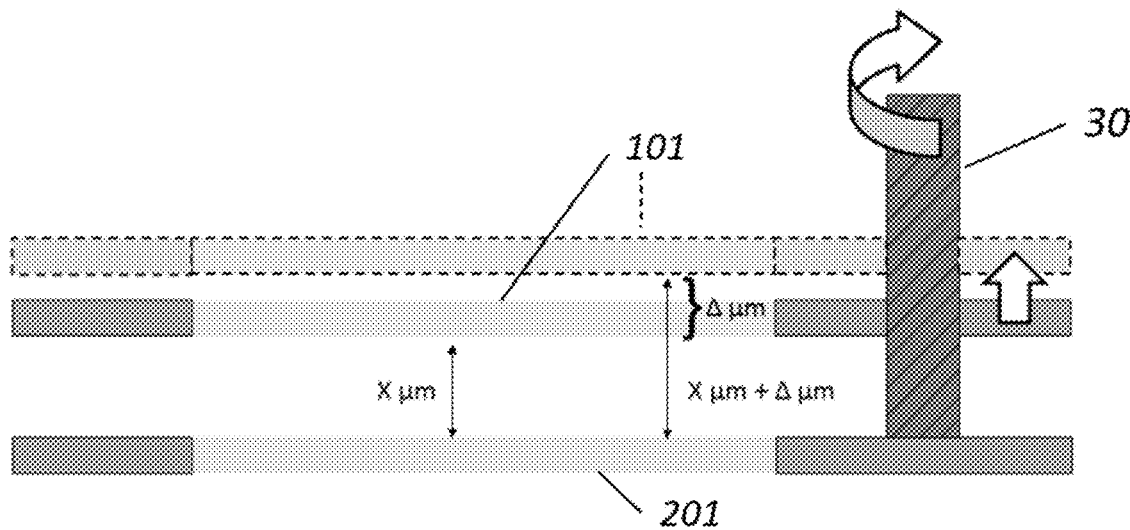

See for example FIG. 2D.

The at least two different depths (c1) provided by the bottom and top measurement window are preferably in the range of about 5 to about 100 μm, more preferably about 10 μm to 40 μm, for example about 15 μm and about 30 μm, or about 10 μm and about 20 μm.

Preferably, the difference between the two different depths (c1) provided by the bottom and top measurement window is at least the size or height of a monolayer of the cells or particles of the sample to be analyzed.

In one embodiment, the counting compartment comprises more than two different depths, which can be provided by a combination of the above embodiments (i) to (iv), such as by more than two steps.

For example, the counting compartment may comprise three different depths.

(c2) The at least one further depth is different from the at least two depths (c1), it is preferably bigger.

In one embodiment, the at least one further depth is the range of about 100 to about 500 μm, such as from about 150 to about 300 μm, for example about 200 μm.

Said third and bigger depth allows reducing/minimizing capillary effects or other flow effects of the sample in the measurement field of the counting compartment, and allows for a simpler rinsing or cleaning afterwards before loading with the next sample.

Furthermore the rinsing or cleaning of the measuring area/field can be done without moving the lid or top part between samples. The third bigger depth is also useful for samples which contain particles bigger than the depth in the measuring area/field, allowing the displacement of these particles from the measuring area during closure of the chamber into the area with the bigger depth, thus avoiding side effects or problems with the closing of the chamber or the chamber depth.

Said at least one further depth is located in the counting compartment or in the area of the measuring window.

Said at least one further depth can be achieved in different ways. For example, the top and/or the bottom measurement window can comprise protrusion(s) in the in the shape of
a strip or band,
cones, cuboids or the like,
said cones, cuboids or the like preferably having fluid-dynamically favorable transitions from the flat surface of the measuring window to the lateral sides protruding into the gap,
or combinations thereof.

For examples, see FIGS. 6A and 6B.

In one embodiment, the counting compartment comprises two different depths, which are in the range of about 5 to about 100 μm (such as about 15 μm and about 30 μm); and the counting compartment comprises the at least one further depth in the range of 100 to 500 μm (such as about 200 μm).

Said three different depths can be achieved in different ways.

In an embodiment, as exemplified in FIG. 6A, the top measurement window comprises one protrusion in only one of the x- or y-direction in the shape of a strip or band which then comprises a step for providing the two different depths of e.g. about 15 μm and about 30 μm.

In an embodiment, as exemplified in FIG. 6B, the top measurement window comprises a plurality of protrusions in the shape of cones, cuboids or the like, wherein each of said plurality of protrusions comprises a step for providing one of the two different or both depths of e.g. about 15 µm and about 30 µm.

In an embodiment, not shown in a Figure, the bottom measurement window comprises said plurality of protrusions in the shape of cones, cuboids or the like, such as described above; or the top and the bottom measurement window comprise said plurality of protrusions in the shape of cones, cuboids or the like.

The inventors have found that not only the depth provided by the top and bottom measurement window has an influence on the capillary effect and flow effects of the sperm sample when loaded, but also the width of the small layers, i.e. the depth of the layer (i.e. the z-direction) and the width (i.e. the x-direction or both the x- and y-direction).

For example, when seen from the top (or from the direction of the camera analyzing the sample from the top),
- if one provides a circular measurement field, then the radius of said circular measurement field is preferably small, preferably less than about 1.5 mm, such as about 1 mm or smaller;
- if one provides a rectangular measurement field, preferably an rectangle (such as a square, trapezium, rhombus or strip), then the sides/edges of said rectangular measurement field are on one axis preferably small, preferably less than about 3.0 mm, such as about 2.0 mm or smaller;
- For example: the rectangle is an equilateral rectangle (such as a square, trapezium, rhombus) wherein the sides/edges of said equilateral rectangular measurement field are less than about 3.0 mm, such as about 2.0 mm or smaller, e.g. less than about 1.5 mm, such as about 1 mm or smaller.
- For example: the rectangle is in the form of a strip or band or the like with the sides/edges of said rectangular measurement field being on one axis less than about 3.0 mm, such as about 2.0 mm or smaller.

Preferably, in the measurement window of the counting compartment measurement field(s) are provided, which are preferably circular or rectangular or combinations thereof, with a radius of less than about 1.5 mm or side lengths of less than about 3.0 mm.

(d) In one embodiment, the counting compartment comprises a movable lid or top part. In this embodiment, counting compartment comprises means for moving the lid or top part, wherein said means comprise magnetic means and optionally spacer.

Examples for magnetic means are permanent electro magnet(s). The magnetic means can be comprised in the lid or top part and/or the bottom part.

Examples for spacer are spring-loaded spacers. The spacer(s) can be comprised in the lid or top part and/or the bottom part.

Furthermore, (micrometer) screws or gauges can be comprised in the lid or top part and/or the bottom part.

In one embodiment, the lid or top part and the bottom part of the counting compartment/chamber of the invention are manufactured by high precision manufacturing. In such embodiment, no (micrometer) screws or gauges are necessary.

In one embodiment, the lid or top part is moved by mechanic means, such as a spindle with an attached motor.

(d) In one embodiment, the counting compartment does not comprise a movable lid or top part. In this embodiment the lid or top part is fixed.

Said embodiment allows a closed system of the counting compartment. However, the lid or top part can be removed, in particular for washing and cleaning.

(a) and (b) The lid or top part and the bottom part are preferably configured such that they form the bottom, lid and side walls of the counting compartment or counting chamber.

In one embodiment, the lid or top part and the bottom part are made of steel, such as stainless steel.

In one embodiment, the lid or top part and the bottom part are made of ceramics or plastic or using a coating of yet another material to provide certain properties to the device or a combination of materials and manufacturing technologies.

(e) The inlet and/or outlet can be part of the lid or top part and/or the bottom part.

(f) and (g) A heating unit is suitable for controlling the temperature of the sample to be analyzed, in particular in case of a semen sample. A positioning unit is suitable for moving the counting compartment. The positioning and heating unit can be separate but also jointed into one system.

In a preferred embodiment, the counting compartment or counting chamber of the present invention is a flow-through counting compartment or counting chamber.

Therefore, the counting compartment or counting chamber of the present invention is provided/configured such that it can be connected with pumps, control units etc.

In one embodiment, the (flow-through) counting compartment further comprises (h) means for controlling the depth of said counting compartment.

Said means for controlling the depth of said counting compartment are preferably sensor(s), such as optical sensor(s), white-light interferometer sensor(s), current sensor(s), capacitive sensor(s) or laser sensor(s), and/or means for z axis-calibration.

In one embodiment, the counting compartment of the present invention, further comprises (j) a grid in one of the measurement windows.

Said grid allows a manual count.

The present invention provides a counting device for analyzing samples comprising spermatozoa.

Said counting device comprises
the counting compartment of the present invention,
a control unit,
filling means,
removing means,
a light microscope and/or a fluorescence microscope,
optionally, sensor(s),
and
processing, analyzing and/or evaluating system and software.

Examples for filling means are an injection pump, injection syringe, flexible-tube pump, dilutors, tubing, An example for removing means is a draw-off pump.

The light microscope and/or the fluorescence microscope is preferably a phase contrast microscope.

In one embodiment, the light microscope and/or the fluorescence microscope comprise a motorized positioning unit, and/or a heating unit.

The counting device optionally comprises sensor(s).

Examples for suitable sensors are:
white-light interferometer sensor,
current sensor, inductive sensor,
capacitive sensor, or
optical sensor.

Said sensor(s) of the counting device are for determining and obtaining the depth(s) of the counting compartment.

An example of the processing, analyzing and/or evaluating system and software is AndroVision® CASA Software (of Minitüb GmbH, Germany).

In one embodiment, the counting device of the present invention, further comprises
a grid in the ocular of the light microscope or in one of the measurement windows of the counting compartment or chamber.

Said grid allows a manual count.

In one embodiment of the counting device, in the flow-through counting compartment said at least two different depths (c1) provided by the bottom and top measurement window are in the range of about 5 to about 100 μm, preferably about 10 μm to 40 μm (such as about 15 μm and about 30 μm), such that the difference between the two different depths (c1) is at least the size or height of a monolayer of the spermatozoa of the sample to be analyzed, and/or said at least one further depth (c2) is in the range of about 100 to about 500 μm, such as about 200 μm.

Preferably, in the measurement window of the counting compartment measurement field(s) are provided, which are preferably circular or rectangular or combinations thereof, with a radius of less than about 1.5 mm or side lengths of less than about 3.0 mm.

The samples are preferably semen samples.

The counting device of the present invention can be designed for the manual or automated use.

In one embodiment, the counting device of the present invention is (fully) automatized.

Further Description of Preferred Embodiments

The method of the present invention was developed due to the following critical features of measuring a sperm sample:
the way of loading the device as well as the quality of the sperm sample can influence the result of such an evaluation;
the speed of closing the flow-through chamber can influence the measurement results;
the time needed for loading and closing is critical and, thus, needs to be controlled or specified otherwise the measurement results can be influenced;
the small depths used in the measurement window of a flow-through chamber can cause capillary effects or other flow effects and, thus, a reduction of sperm present in the measuring area, when closing the chamber;
the inherent characteristics of spermatozoa can influence the measurement results, such as a spermatozoa' rheotaxis can result in an unrepresentative distribution of the sperm in the sample (such as accumulation) at the top and bottom walls of the counting chamber and the respective measuring windows, in particular within longer time periods between the loading and closing;

The present invention provides a method for analyzing sperm samples which allows a reliable measurement of said sperm samples, especially in an automated setting and using a flow-through counting chamber.

The counting compartment of the present invention was developed due to the following critical features of single-use or one-way devices, which are for example:

difficulty that the indicated depth for quantitative evaluation of a sample is maintained over thousands of pieces;
the way of loading the device as well as the quality of the sample can influence the result of such an evaluation;
requirement of evenness or planarity of each of the disposable plates/glasses;
requirement to adjust the focus level from one disposable device to the next disposable device due to varying material thickness of the plates/glasses;
requirement for highly trained and educated lab staff to pipette correctly volumes as small as 2.7 μL for loading the sample into the disposable device;
sample compatibility (such as sperm compatibility) of the materials;
for each sample, a new one-way device needs to be used;
during storage pre-assembled disposable counting chambers develop stains and other visible artefacts on the inside of the sample chamber which makes sample analysis difficult or impossible;
will the cells of the sperm sample be evenly distributed in the counting compartment?

The present invention provides a counting compartment or chamber and respective counting device which
can be permanently used, but can also be used once (or one day),
reliably measures sperm samples, such as the number of sperm cells in said spec n sample, or the concentration and motility of sperm samples,
can be used in a simple and automated way,
keeps the same focus level between samples,
reduces or minimizes flow effects/the capillary effects in the sample,
allows for simple rinsing and cleaning.

The counting compartment or chamber and respective counting device of the present invention can be used manually and in an automated manner. In the following an automated embodiment is further explained:

Set-Up of the Counting Compartment or Chamber

The counting compartment or chamber includes a bottom and lid part. The lid part includes micrometer screws or gauges and a measurement window. The bottom part includes a similar configured measurement window. Furthermore, magnetic means and one or more spacers are integrated in the bottom part. The bottom part furthermore includes an outlet area.

Figure 3A:
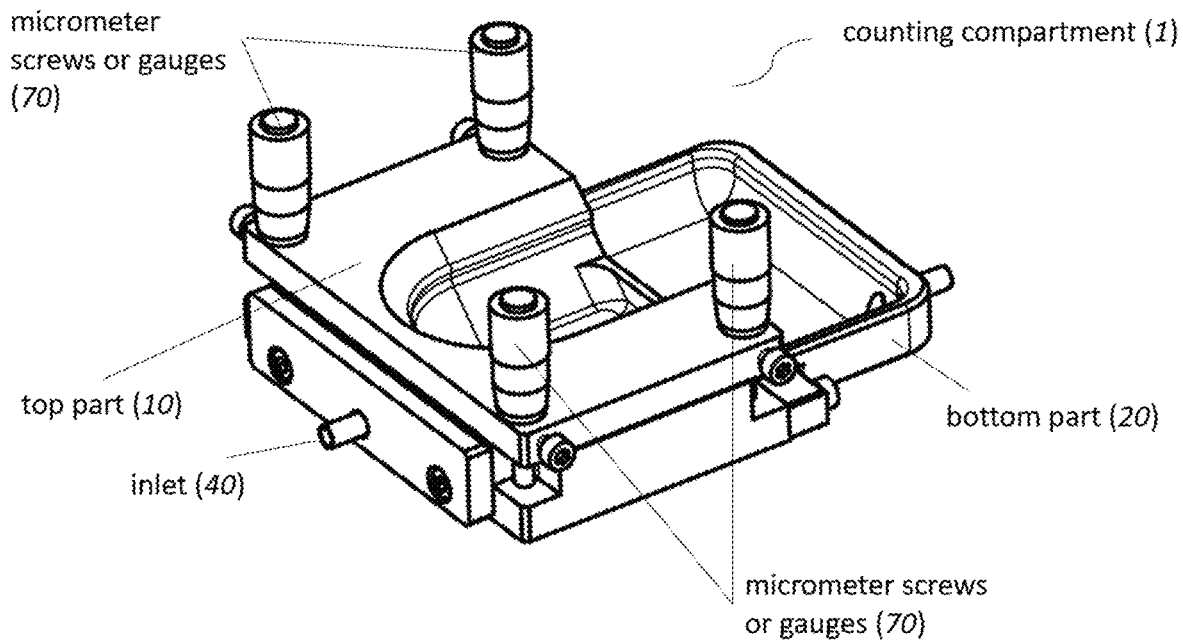
FIGS. 3A-3C. A preferred embodiment of the counting compartment.
(A) The top or lid part (10) comprising a top measurement window (101) and micrometer screws or gauges (70), wherein the top or lid part (10) is situated on the bottom part (20).
(B) The bottom part (20) comprising a bottom measurement window (201), permanent electro magnets (301), spacer (302) and an outlet (50).
(C) The top or lid part (10) comprising a top measurement window (101).
Figure 3B:
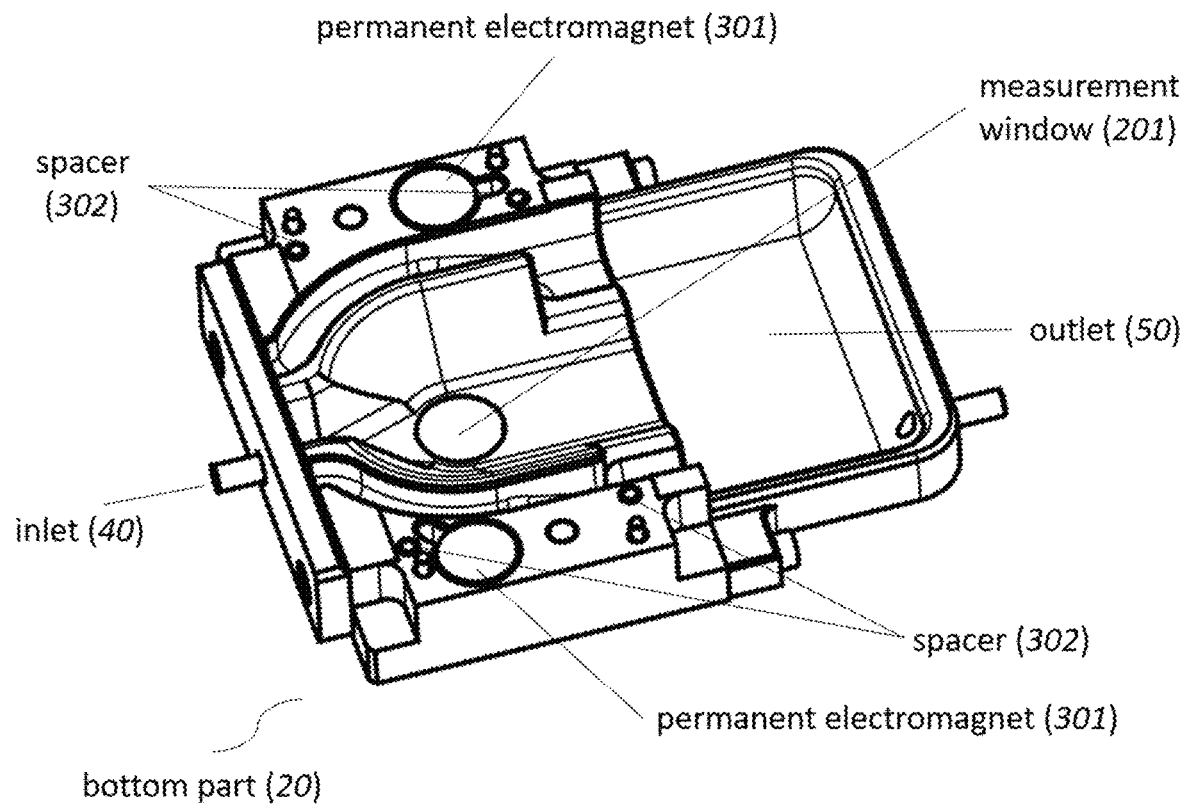
Figure 3C:
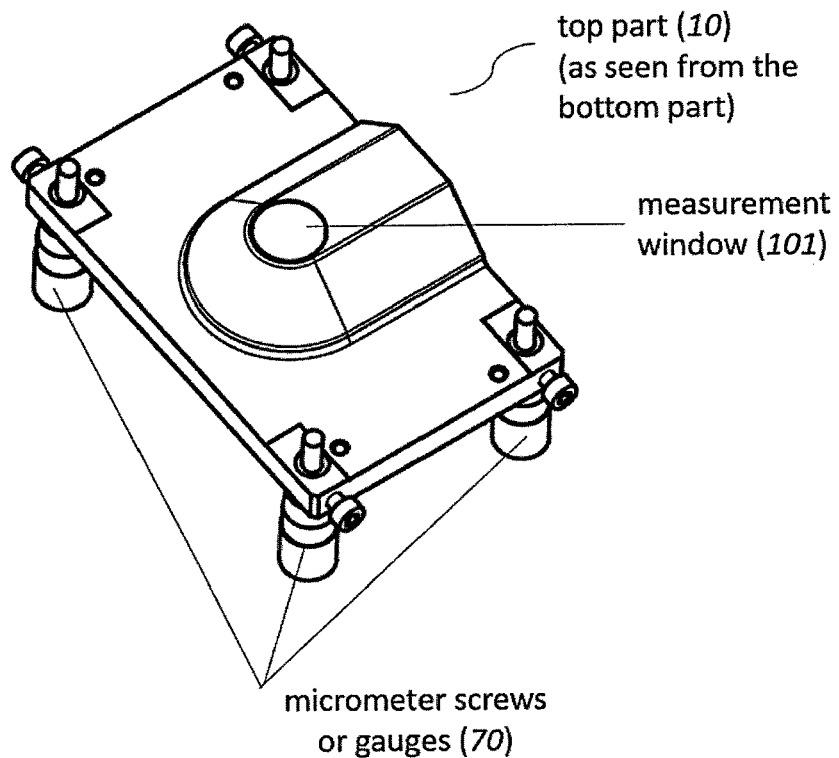

For details, please see FIGS. 3A to 3C.

The Measurement Window

The measurement windows (made of glass or plastic) are configured such that in the middle there is a step (for example, in the range of 5 to 10 μm, such as a 5 μm, or 7.5 μm high step; or for example, in the range of 5 to 15 μm, such as a 7.5 μm, or 15 μm high step). When the measurement windows are set into the lid and bottom part, the measurement windows are aligned/oriented that both steps are congruent (i.e. super-imposed) and in the direction of the sample flow. The steps are super-imposed, thereby forming two different heights/depths of the counting compartment, which differ in height by the sum of the steps in the measurement windows (for example, the sum can be in the range of 10 to 20 μm, such as 10 μm or 15 μm; or for example, the sum can be in the range of 10 to 40 μm, such as 15 μm or 30 μm) (see FIG. 2A).

Periphery of the Counting Compartment or Chamber (i.e. the Counting Device)

Figure 4:
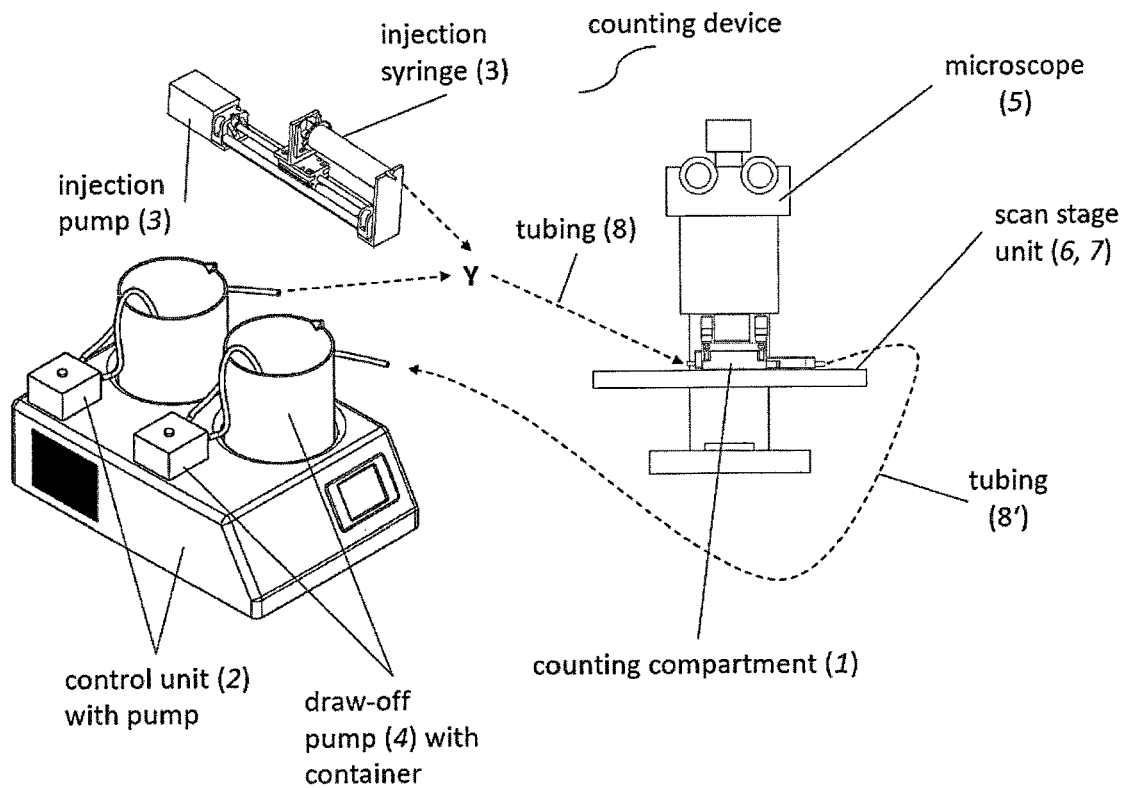
FIG. 4. An exemplary embodiment of the counting device.
The counting device comprising a phase contrast light microscope (5), scan stage unit (6,7), control unit (2) with pump, draw-off pump with container (4), injection pump (3), injection syringe for sample (3). The counting device is connected to a processing, analyzing and/or evaluating system and software (9), in particular AndroVision® CASA Software (Minitüb GmbH, Germany).

For use, the counting compartment is positioned on a heated motorized positioning unit underneath a light microscope with negative phase contrast (see FIG. 4). Furthermore, the counting compartment is connected to a draw-off pump, a control unit, an injection pump (with e.g. sample syringe connected thereto).

Mode of Operation of the Counting Compartment or Chamber

The functional core of the counting compartment is the volume which is formed by the overlapping measurement windows of lid and bottom part. During manufacturing of the counting compartment, the distance of both measurement windows to each other is adjusted, namely planparallel to each other and at a determined distance, by the micrometer screws/gauges integrated in the lid. The distance between the two measurement windows is calibrated and adjusted with a continuous white-light interferometry measurement. Generally, depths between about 5 µm to 100 µm, preferably 10 to 40 µm are set (adjusted). During operation the closed lid is kept at the set distance from the bottom by means of the micrometer screws/gauges.

Opening and closing of the counting compartment is carried out by magnetic means and spacers (springs), such as permanent electro magnets located in the bottom part.

For example, the magnetic means can function in the following way: If no electric current is applied, the lid is pulled towards the bottom, such that the counting compartment is closed. If electric current is applied, the magnetic means lose their holding force, such that the lid part is lifted by the spacers (springs), and the counting compartment is open. In case the electric power is turned off, the counting compartment closes.

Liquids are only loaded when the counting compartment is open. The loading usually is carried out via silicone tubing, wherein a y-angle, which is located upstream of the counting compartment, allows sample liquid and washing liquid (such as diluent in case of semen samples) to flow into the inlet of the counting compartment. The y-angle can be replaced by an automated fluid management system.

Injection of the sample is carried out using an injection pump, in which a milliliter syringe filled with sample liquid is placed. The washing or rinsing liquid is pumped into the counting compartment when needed via a flexible-tube pump located e.g. in the housing of the control unit. Said pump uses washing liquid (such as diluent in case of semen samples).

Downstream of the counting compartment is a draw-off pump, which is connected to the outlet via silicone tubing and which draws off waste or superfluous liquid from the counting compartment.

The whole process is controlled by a (central) control unit.

Said central control unit can be connected to and communicate with a processing, analyzing and/or evaluating system and software, such as Androvision®, for further automation. Then, only one start signal could be required.

Mode of Operation of the Step-Measurement Windows

Preferably, a processing, analyzing and/or evaluating system and software, such as Androvision®, is used.

Figure 5:
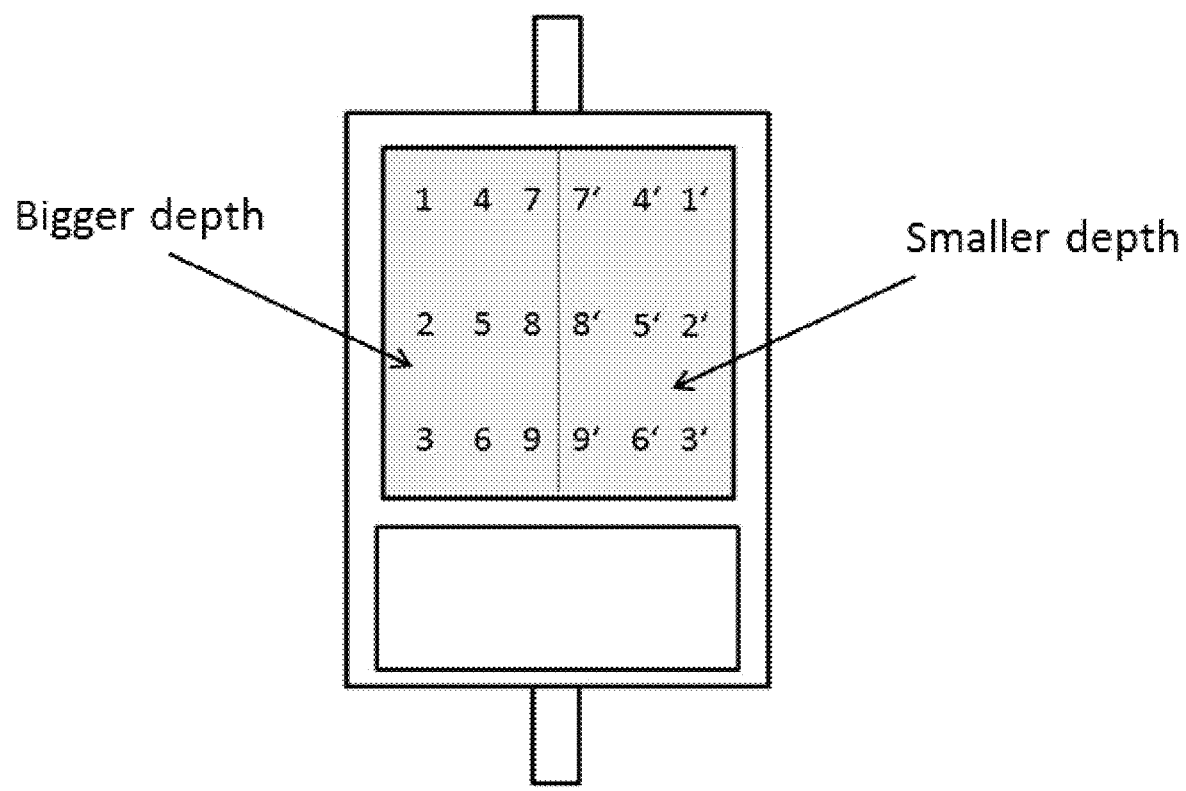
FIG. 5. Schematic view of the arrangement of measurement fields during an analysis with an evaluating system and software.
(in particular AndroVision® CASA Software).
The shown scheme serves as example for a measuring pattern using several analysis fields on each side of the counting chamber. Any combination of amount of fields per analysis and location of such fields is possible.

The bigger depth is used for determining the cell number/count (e.g. sperm number) and the motility patterns of the sperm. See e.g. FIG. 5.

Furthermore, in the smaller measurement depth, a morphological analysis of sperm cells is carried out.

Advantages of the Counting Compartment or Chamber precise measurement of concentration of a sample, such as sperm concentration, and further features of the sample, such as sperm motility;

provides for each aspect of the sperm analysis the ideal chamber depth: sperm number and motility patterns are measured in a greater gap to capture an optimum number of sperm per analysis field as well as to provide ideal conditions for the sperm to show their motility behavior. The smaller gap is used to bring all sperm into a narrow focus range, optimizing the image quality for morphological analysis;

can be re-used permanently, thereby reducing costs in a routine laboratory use;

automatized use, thereby avoiding errors of the user;

does not require pipetting small volumes (between 2 and 3 µL) to fill the capillary gap of a standard counting chamber;

uses bigger volumes of ejaculate (500 µL instead of 100 µL) for preparing the sperm sample to be analyzed which reduces the probability of pipetting errors and minimizes their effects on sperm counts;

can be connected and integrated with a processing, analyzing and/or evaluating system and software (such as Androvision® CASA system of Minitüb GmbH, Germany).

The counting chamber providing three different depths provides even further advantages:

said third bigger depth allows reducing/minimizing any capillary effects or other flow effects of the sample, and allows for a simpler rinsing or cleaning.

The following examples illustrate the present invention without, however, limiting the same thereto.

EXAMPLES

Example 1

Measurement Conditions

The counting compartment can be used for sample analyses after cleaning and rinsing.

Furthermore, the compartment has to warm up on a certain temperature which can generally be achieved by using a heating unit integrated into the microscope. For semen samples the temperature should simulate physiological conditions (e.g. between 35° C. and 39° C.).

Cleaning can be conducted by using alcoholic derivatives and distilled water; rinsing can be conducted by using a sperm-friendly medium such as BTS semen extender in case of semen samples. The amount of rinsing liquid should be sufficiently chosen in order to remove the amount of sample material in the counting compartment.

The counting compartment has to be opened for rinsing i.e. the lid or top part is in open position.

After homogenizing a sufficient amount of sample can be injected into the counting compartment. The counting compartment has to be open during sample injection. Analyses can follow after closing the counting compartment.

After finishing analyses the compartment is opened again and rinsed for the next sample.

The procedure starts from the beginning but without the cleaning step which is only necessary after finishing the last semen analysis of the day or before using the compartment for the first time on a given day.

Example 2

Sample Treatment

In case of semen samples, the raw ejaculate is appropriately diluted with extenders, such as Androhep® Plus (Minitüb GmbH, Germany), Androstar® Plus (Minitüb GmbH, Germany), M III® (Minitüb GmbH, Germany) or BTS (Minitüb GmbH, Germany), shortly after collecting the ejaculate. For example, an appropriate dilution can be one part raw ejaculate and nine parts of extender, depending on the animal species and expected semen concentration of the ejaculate.

Homogenization of such a diluted sample, especially before using the counting compartment, can be conducted manually or mechanically.

Manual homogenization includes shaking the sample and/or turning the sample in a container.

Mechanical homogenization includes the usage of a vortex mechanical mixer or a magnetic stirrer or similar devices.

The features disclosed in the foregoing description, in the claims and/or in the accompanying drawings may, both separately and in any combination thereof, be material for realizing the invention in diverse forms thereof.

The invention claimed is:

1. A method for analyzing samples comprising spermatozoa, said method comprising the steps of:
   (1) providing a sample comprising spermatozoa to be analyzed;
   (2) providing a flow-through counting compartment, said counting compartment comprising
      (a) a lid or top part comprising a top measurement window;
      (b) a bottom part comprising a bottom measurement window, wherein the movable lid or top part and the bottom part are configured such that they form the bottom, lid and side walls of the counting compartment;
      (b1) wherein one or both of the lid or top part and the bottom part are movable;
      (c) two different depths provided by the bottom measurement window and the top measurement window in the range of about 5 to about 100 µm,
         wherein the two different depths provided by the bottom measurement window and the top measurement window are achieved by
            (i) the bottom measurement window and/or the top measurement window comprise step(s); or
            (ii) one of the bottom measurement window and the top measurement window is placed with inclination; or
            (iii) one of the bottom measurement window and the top measurement window is placed parallel to the other of the bottom measurement window and the top measurement window and is provided with an inclined plane, wherein the inclined plane faces the other of the bottom measurement window and the top measurement window; or
            (iv) moving the lid or top part and/or the bottom part of the counting compartment,
         and wherein the counting compartment comprises at least one further depth that is different from the two depths of (c), and said at least one further depth is in the range of about 150 to about 500 µm;
      (d) optionally, means for moving the lid or top part; and
      (e) an inlet and outlet located at opposite sides of the counting compartment;
   (3) loading the counting compartment with the sample, wherein the lid or top part is in open position;
   (4) closing the counting compartment by closing the lid or top part;
      wherein a time period is carried out between the end of the loading step (3) and the closing step (4), which is less than 1s,
   (5) determining a sample value to be measured at the first depth of the two different depths,
      optionally, determining further sample characteristics at said first depth of the two different depths;
   (6) optionally, determining further sample characteristics at the second depth of the two different depths,
   (7) opening the counting compartment by opening or lifting the lid or top part;
   (8) rinsing the counting compartment and thereby removing the sample,
   wherein the sample value to be measured in step (5) is the number of spermatozoa or concentration of spermatozoa.

2. The method of claim 1, wherein step (5) comprises determining further sample characteristics at said first depth of the two different depths, wherein said further sample characteristics are qualitative characteristics of the sperm contained in the sample or morphological characteristics of the sperm or combinations thereof.

3. The method according to claim 1, wherein the time period between the end of the loading step (3) and the closing step (4) is 300 ms or less.

4. The method according to claim 1, wherein in the counting compartment
   the means for moving the lid or top part (d) comprise magnets and optionally a spacer; and
   the bottom measurement window or top measurement window is made of a transparent material.

5. A counting compartment for analyzing samples comprising spermatozoa, said counting compartment comprising:
   (a) a lid or top part comprising a top measurement window, said lid or top part being movable;
   (b) a bottom part comprising a bottom measurement window, wherein the movable lid or top part and the bottom part are configured such that they form the bottom, lid and side walls of the counting compartment;
      (b1) wherein one or both of the lid or top part and the bottom part are movable:
   (c1) two different depths provided by the bottom measurement window and the top measurement window in the range of about 5 to about 100 µm,
      wherein the two different depths provided by the bottom measurement window and the top measurement window are achieved by
         (i) the bottom measurement window and/or the top measurement window comprise step(s); or
         (ii) one of the bottom measurement window and the top measurement window is placed with inclination; or
         (iii) one of the bottom measurement window and the top measurement window is placed parallel to the other of the bottom measurement window and the top measurement window and is provided with an inclined plane, wherein the inclined plane faces the other of the bottom measurement window and the top measurement window; or
         (iv) moving the lid or top part and/or the bottom part of the counting compartment,
   (c2) at least one further depth which is different from the two depths of (c1), said at least one further depth being bigger, and being located in the counting compartment or in the area of the measuring windows;
(d) means for moving the lid or top part; and
(e) an inlet and outlet located at opposite sides of the counting compartment.

6. The counting compartment of claim 5, which is a flow-through counting compartment.

7. The counting compartment according to claim 5, wherein
the bottom measurement window or the top measurement window is made of a transparent material.

8. A counting device for analyzing samples comprising spermatozoa, said counting device comprising:
a counting compartment comprising:
(a) a lid or top part comprising a top measurement window, said lid or top part being movable;
(b) a bottom part comprising a bottom measurement window, wherein the movable lid or top part and the bottom part are configured such that they form the bottom, lid and side walls of the counting compartment;
(b1) wherein one or both of the lid or top part and the bottom part are movable:
(c1) two different depths provided by the bottom measurement window and the top measurement window in the range of about 5 to about 100 μm,
wherein the two different depths provided by the bottom measurement window and the top measurement window are achieved by
(i) the bottom measurement window and/or the top measurement window comprise step(s); or
(ii) one of the bottom measurement window and the top measurement window is placed with inclination; or
(iii) one of the bottom measurement window and the top measurement window is placed parallel to the other of the bottom measurement window and the top measurement window and is provided with an inclined plane, wherein the inclined plane faces the other of the bottom measurement window and the top measurement window; or
(iv) moving the lid or top part and/or the bottom part of the counting compartment, (c2) at least one further depth which is different from the two depths of (c1), said at least one further depth being bigger, and being located in the counting compartment or in the area of the measuring windows;
(d) optionally, means for moving the lid or top part; and
(e) an inlet and outlet located at opposite sides of the counting compartment,
a control unit connected to the counting compartment,
filling means connected to the inlet of the counting compartment,
removing means connected to the outlet of the counting compartment,
a microscope, and
a scan stage unit for positioning the counting compartment underneath the microscope,
wherein the control unit is programed to fill, and/or remove from, the counting compartment.

9. The counting device of claim 8, wherein in the counting compartment
said two different depths are such that the difference between the two different depths is at least the size or height of a monolayer of the spermatozoa of the sample to be analyzed;
and/or said at least one further depth (c2) is in the range of about 150 to about 500 μm.

10. The counting compartment according to claim 5, wherein in the measurement window measurement field(s) are provided, which are circular or rectangular or combinations thereof, with a radius of less than about 1.5 mm or side lengths of less than about 3.0 mm.

11. The method according to claim 1, further comprising positioning the counting compartment by a positioning unit and/or heating the sample in the counting compartment by a heating unit.

12. The method according to claim 1, comprising determining further sample characteristics at the second depth of the two different depths, wherein the further sample characteristics at the second depth of the two different depths are qualitative characteristics of the sperm contained in the sample or morphological characteristics of the sperm or combinations thereof.

* * * * *